United States Patent [19]
Suzuki et al.

[11] Patent Number: 5,730,953
[45] Date of Patent: Mar. 24, 1998

[54] TRIS(SUBSTITUTED PHENYL) BISMUTH DERIVATIVES

[75] Inventors: Hitomi Suzuki, Matsuyama; Koichi Maeda, Tokyo; Keizo Tanikawa; Katsuaki Miyaji, both of Funabashi, all of Japan

[73] Assignee: Nissan Chemical Industries, Ltd., Tokyo, Japan

[21] Appl. No.: 596,371

[22] PCT Filed: Aug. 22, 1994

[86] PCT No.: PCT/JP94/01381

§ 371 Date: Mar. 19, 1996

§ 102(e) Date: Mar. 19, 1996

[87] PCT Pub. No.: WO95/06053

PCT Pub. Date: Mar. 2, 1995

[30] Foreign Application Priority Data

Aug. 23, 1993 [JP] Japan ................................. 5-207970
Jul. 19, 1994 [JP] Japan ................................. 6-166619

[51] Int. Cl.[6] ................................. A61K 49/04
[52] U.S. Cl. .................. 424/9.42; 424/900; 514/60; 556/69; 556/70
[58] Field of Search .................. 556/69, 70; 424/9.42, 424/900; 514/60

[56] References Cited

U.S. PATENT DOCUMENTS 5,536,424  7/1996  Delfort et al. ................... 508/401

FOREIGN PATENT DOCUMENTS 06128508  5/1994  Japan.
WO 90/03036  3/1990  WIPO.

OTHER PUBLICATIONS

Horner et al., *Phosphorus Sulfur*, 14(2):253–260, (1983).

Gielen et al. *Organic Mass Spectrometry* 19(12):647–649, (1984).

Polymer, vol. 33, No. 8, pp. 1724–1730, Jan. 1, 1992, F. Ignatious, et al., "Organobismuth Polymers as X–Ray Contrast Materials: Synthesis, Characterization and Properties".

Dental Materials, vol. 8, pp. 54–59, Jan. 1992, H.R. Rawls, et al., "Cytotoxicity Evaluation of a New Radiopaque Resin Additive–Triphenyl Bismuth".

Polymer Preprints, vol 30, No. 2, pp. 185–186, Sep. 1989, Y. Delaviz, et al., "Polymers with Covalently Bound Bismuth as X–Ray Contrast Materials".

*Primary Examiner*—Gary E. Hollinden
*Attorney, Agent, or Firm*—Oblon, Spivak, McClelland, Maier & Neustadt, P.C.

[57] ABSTRACT tris(substituted phenyl) bismuth compounds of formula (I) and pharmaceutically acceptable salts thereof are useful x-ray radiographic imaging agents:

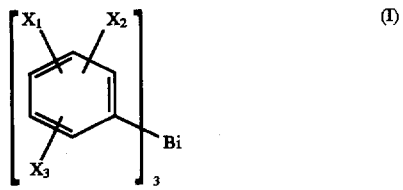

wherein $X_1$, $X_2$ and $X_3$ are as defined in the specification.

11 Claims, No Drawings

TRIS(SUBSTITUTED PHENYL) BISMUTH DERIVATIVES

TECHNICAL FIELD

The present invention relates to novel substituted triphenylbismuth derivatives and, if any, pharmaceutically acceptable salts thereof which have excellent radiographic contrasting ability, processes of producing them and pharmaceutical compositions for medical inspection containing them as an ingredient.

BACKGROUND ART

Radiography, especially X-ray radiography, has long been used widely as a medical technique for diagnosis and analysis of various diseases. However, not a few parts of the body such as the vasculature, the urinary tract, the gallbladder, the bile duct and the cerebrospinal cavity require a contrast medium for a higher resolution. In particular, angiography is almost indispensable to diagnosis of various angiopathies, mainly in the tissues of extremities and the brain, and medical need for angiography is increasing. As contrast media for angiography, 2,4,6-triiodobenzoic acid derivative type compounds represented by iopamidol, iohexol and ioxaglate are now in use. However, contrast media with a higher contrasting ability are required for diagnosis in an increasing number of cases. In addition, under the present the side effects of these media for injection, such as heat and pain at the time of injection due to their osmotic pressures higher than that of the blood, and nausea, vomiting and eruption, which are thought as peculiar to iodine compounds, are regarded as questionable.

As a method of improving contrasting ability, compounds having more iodine atoms introduced per molecule are conceivable, however, they seem to have many problems in practical use due to their chemical instability and difficulties in their production. On the other hand, some compounds containing atoms with a nucleus larger than that of an iodine atom, are expected to exhibit a higher contrasting ability commensurate with their radiation shielding power. However, the enhanced chemical instability accompanied by enlargement of atomic nuclei, difficulties in their production and the toxicity are seriously problematic in practical use of these compounds as a contrast medium.

DISCLOSURE OF INVENTION

As a result of extensive searches, the present inventors found that the tris(substituted phenyl)bismuth derivatives and their pharmaceutically acceptable salts of the present invention, which are different from any compound disclosed in the documents (a) to (c), are all chemically stable and biologically safe, and exhibit an excellent contrasting ability in X-ray radiography, that in particular, the water soluble tris(substituted phenyl)bismuth derivatives having a hydroxyl group at the ω-terminal of a substituent on a benzene ring and their pharmaceutically acceptable salts exhibit a high contrasting ability in X-ray radiography and that they can be used as an ingredient to provide a safe and useful contrast medium for X-ray radiography of the vasculature, the urinary tract, the gallbladder, the bile duct or the cerebrospinal cavity which can obviate the problematic side effects of conventional media attributable to iodine. On the basis of these discoveries, the present inventors have achieved the present invention.

The present invention provides tris(substituted phenyl) bismuth derivatives of the general formula (I) or, if any, pharmaceutically acceptable salts thereof:

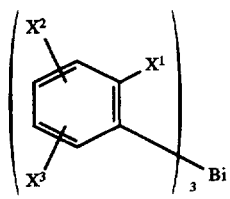

{wherein $X^1$ is $Y^1$—$NR^1R^2$ [wherein $Y^1$ is —$SO_2$— or

and each of $R^1$ and $R^2$ is, independently of each other, a hydrogen atom, a $C_{1-4}$ alkyl group or A—Z (wherein A is an alkylene chain which has 2–6 carbon atoms in total and may have a branch having at least two carbon atoms, and Z is $OR^3$ (wherein $R^3$ is $SiR^4R^5R^6$ (wherein each of $R^4$, $R^5$ and $R^6$ is, independently of one another, a $C_{1-4}$ alkyl group or a phenyl group), a hydrogen atom or a $C_{1-4}$ alkyl group) or $NR^7R^8$ (wherein each of $R^7$ and $R^8$ is, independently of each other, a hydrogen atom or a $C_{1-4}$ alkyl group)) provided that the case where $R^1$ and $R^2$ are both hydrogen atoms is excepted],

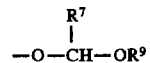

(wherein $R^9$ is a $C_{1-4}$ alkyl group, and $R^7$ is the same as defined above) or $Y^2$—A—Z [wherein $Y^2$ is an oxygen atom, —$S(O)_n$— (wherein n is an integer of 0 or 2) or

(wherein $R^1$ is the same as defined above), and A and Z are the same as defined above], and each of $X^2$ and $X^3$ is, independently of each other, a hydrogen atom or any substituent defined above with respect to $X^1$, processes of their production and a pharmaceutical compositions for medical inspection containing them as an ingredient.

$X^1$, $X^2$ and $X^3$ in the compounds of the present invention represented by the above general formula (I) are explained below.

$X^1$ is an N-alkyl- or N,N-dialkyl-sulfamoyl or -carbamoyl group represented by —$SO_2NHR^{1'}$, —$SO_2NR^{1'}R^{2'}$, —$C(O)NHR^{1'}$ or —$C(O)NR^{1'}R^{2'}$ (wherein each of $R^{1'}$ and $R^{2'}$ is, independently of each other, a methyl group, an ethyl group, a n-propyl group, an i-propyl group, a n-butyl group, an i-butyl group, a sec-butyl group or t-butyl group), an N-ω-substituted alkyl-, N,N-alkyl-ω-substituted alkyl- or N,N-di-ω-substituted alkyl-sulfamoyl or -carbamoyl group represented by $SO_2$—NHA'—Z', $SO_2$—$NR^{1'}$(A'—Z') $SO_2N$(A'—Z')(A"—Z"), —C(O)NH(A'—Z'), —C(O)$NR^{1'}$(A'—Z') or —C(O)N(A'—Z')(A"—Z") [wherein $R^{1'}$ is an alkyl group as defined above, each of Z' and Z" is, independently of each other, a silyloxy group such as a trimethylsilyloxy group, a triethylsilyloxy group, a t-butyldimethylsilyloxy group or a t-butyldimethylsilyloxy group, a hydroxy group, a methoxy group, an ethoxy group, a n-propoxy group, an i-propoxy group, a n-butoxy group, an i-butoxy group, a sec-butoxy group, a t-butoxy group, an amino group, or an N-alkylamino or N,N-dialkylamino group represented by NHR⁷' or NR⁷R⁸' (wherein each of R⁷' and R⁸' is, independently of each other, a methyl group, an ethyl group, a n-propyl group, an i-propyl group, a n-butyl group, an i-butyl group, a sec-butyl group, or a t-butyl group), and each of A' and A" is, independently of each other, an ethylene chain, a propylene chain, a butylene chain, a pentylene chain, a hexylene chain or an alkylene chain which has 3–6 carbon atoms in total and may be substituted with a methyl group, an ethyl group, a n-propyl group, an i-propyl group, a n-butyl group, an i-butyl group, a sec-butyl group or a t-butyl group at any position of the alkylene chain], a methoxymethyloxy group, an ethoxymethyloxy group, a n-propoxymethyloxy group, an i-propoxymethyloxy group, a n-butoxymethyloxy group, an i-butoxymethyloxy group, a sec-butoxymethyloxy group, a t-butoxymethyloxy group, an alkoxy-alkyl substituted-methyloxy group which is obtainable by substituting the above-mentioned alkoxymethyloxy group with a methyl group, an ethyl group, a n-propyl group, an i-propoxy group, a n-butyl group, an i-butyl group, sec-butyl group or a t-butyl group at the methylene site, or an ω-substituted alkyleneoxy, ω-substituted alkylenethio, ω-substituted alkylenesulfonyl, N-ω-substituted alkylamino or N,N-di-ω-substituted alkylamino group represented by O—A'—Z', —S—A'—Z', —SO₂—A'—Z', NHR¹'—A'—Z' or NR¹' (A'—Z') [wherein A', Z' and R¹' are the same as defined above].

Each of X² and X³ is, independently of each other, a hydrogen atom or any substituent defined above with respect to X¹.

Among the compounds of the present invention represented by the general formula (I), those highly water-soluble are the tris(substituted phenyl)bismuth derivatives of the general formula (I) those wherein X¹ is Y¹—NR¹R² {wherein Y¹ is —SO₂—, and each of R¹ and R² is, independently of each other, a $C_{1-4}$ alkyl group or A—Z¹ [wherein A is an alkylene chain which has 2–6 carbon atoms in total and may have a branch having at least two carbon atoms, and Z¹ is OR³ (wherein R³ is SiR⁴R⁵R⁶ (wherein each of R⁴ R⁵ and R⁶ is, independently of one another, a $C_{1-4}$ alkyl group or a phenyl group), a hydrogen atom or a $C_{1-4}$ alkyl group)]} or

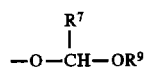

(wherein R⁷ is a hydrogen atom or a $C_{1-4}$ alkyl group, and R⁹ is a $C_{1-4}$ alkyl group), and each of X² and X³ is, independently of each other, a hydrogen atom or any substituent defined above with respect to X¹, and, if any, pharmaceutically acceptable salts, and therefore, they are favorable compounds which can be used as contrast media in a wide variety of formulations such as angiographic contrast media for injection, which are in high medical demand in recent years.

Among the tris(substituted phenyl)bismuth derivatives represented the general formula (I) and, if any, the pharmaceutically acceptable salts of the present invention, typical compounds are listed in Table I, as examples. However, it should be understood that the present invention is by no means restricted to these specific examples.

In Table I, n means normal, i means iso, sec means secondary, t means tertiary, Me means a methyl group, Et means an ethyl group, Pr means a propyl group, and Bu means a butyl group.

TABLE 1

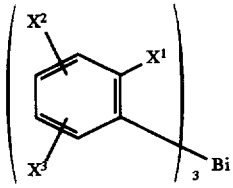

| No. | X¹ | X² | X³ |
|---|---|---|---|
| 1 | SO₂NEt₂ | H | H |
| 2 | CONEt₂ | H | H |
| 3 | OCH₂OCH₃ | H | H |
| 4 | SO₂N(CH₂CH₂OH)₂ | H | H |
| 5 | SO₂N(CH₂CH₂OSiʰBuMe₂)₂ | 4-SO₂N(CH₂CH₂OSiʰBuMe₂)₂ | H |
| 6 | SO₂N(CH₂CH₂OH)₂ | 4-SO₂N(CH₂CH₂OH)₂ | H |
| 7 | SO₂NH(CH₂CH₂OH) | H | H |
| 8 | SO₂NMe(CH₂CH₂OH) | H | H |
| 9 | SO₂NMe(CH₂CH₂OH) | 4-SO₂NMe(CH₂CH₂OH) | H |
| 10 | SO₂N(CH₂CH₂OH)₂ | 4-SO₂NMe(CH₂CH₂OH) | H |
| 11 | SO₂N(CH₂CH₂OH)₂ | 4-SO₂NEt(CH₂CH₂OH) | H |
| 12 | SO₂N(CH₂CH₂OH)₂ | 4-SO₂NⁿPr(CH₂CH₂OH) | H |
| 13 | SO₂N(CH₂CH₂OH)₂ | 4-SO₂N(CH₂CH₂OH)₂ | 5-OCH₂CH₂OH |
| 14 | SO₂N(CHMeCH₂OH)₂ | 4-SO₂N(CHMeCH₂OH)₂ | H |
| 15 | SO₂N(CHEtCH₂OH)₂ | 4-SO₂N(CHEtCH₂OH)₂ | H |
| 16 | SO₂N[(CH₂)₂CH₂OH]₂ | 4-SO₂N[(CH₂)₂CH₂OH]₂ | H |
| 17 | SO₂N(CH₂CH₂OH)₂ | 4-O(CH₂)₂OH | 5-OCH₂CH₂OH |
| 18 | SO₂N(CH₂CH₂OH)₂ | 4-OCH₂OMe | H |
| 19 | SO₂N(CH₂CH₂OH)₂ | 4-OCHMeCH₂OH | H |
| 20 | SO₂N(CH₂CH₂OH)₂ | 4-SO₂N(CH₂CH₂OH)₂ | 5-OCH₂OMe |
| 21 | SO₂N(CH₂CH₂OH)₂ | 4-S(CH₂)₂OH | H |
| 22 | SO₂N(CH₂CH₂OH)₂ | 4-SO₂(CH₂)₂OH | H |
| 23 | SO₂N(CH₂CH₂OH)₂ | 4-S(CH₂)₃OH | H |
| 24 | SO₂N(CH₂CH₂OH)₂ | 4-SO₂(CH₂)₃OH | H |
| 25 | SO₂N(CH₂CH₂OH)₂ | 4-NHCH₂CH₂OH | H |

TABLE 1-continued

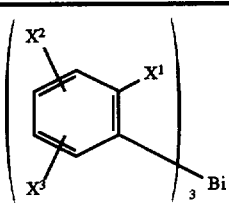

| No. | X¹ | X² | X³ |
|---|---|---|---|
| 26 | SO₂N(CH₂CH₂OH)₂ | 4-NMeCH₂CH₂OH | H |
| 27 | SO₂N(CH₂CH₂OH)₂ | 4-NEt(CH₂CH₂OH) | H |
| 28 | SO₂N(CH₂CH₂OH)₂ | 4-NⁿPr(CH₂CH₂OH) | H |
| 29 | SO₂N(CH₂CH₂OH)₂ | 4-N(CHMeCH₂OH)₂ | H |
| 30 | SO₂N(CH₂CH₂OH)₂ | 4-N(CH₂CH₂OH)₂ | H |
| 31 | SO₂N(CH₂CH₂OH)₂ | 4-N[(CH₂)₃OH]₂ | H |
| 32 | SO₂N(CH₂CH₂OH)₂ | 4-N[(CH₂)₄OH]₂ | H |
| 33 | SO₂N(CH₂CH₂OH)₂ | 4-N(CH₂CH₂NH₂)₂ | H |
| 34 | SO₂N(CH₂CH₂OH)₂ | 4-N(CH₂CH₂NHMe)₂ | H |
| 35 | SO₂N(CH₂CH₂OH)₂ | 4-N(CH₂CH₂NMe₂)₂ | H |
| 36 | SO₂N(CH₂CH₂OH)₂ | 4-N(CH₂CH₂NEt₂)₂ | H |
| 37 | CON(CH₂CH₂OH)₂ | H | H |
| 38 | CONH(CH₂CH₂OH) | H | H |
| 39 | CON(CH₂CH₂OH)₂ | 4-CON(CH₂CH₂OH)₂ | H |
| 40 | CONMe(CH₂CH₂OH) | 4-CONMe(CH₂CH₂OH) | H |
| 41 | CON(CHMeCH₂OH)₂ | 4-CON(CHMeCH₂OH)₂ | H |
| 42 | CON[(CH₂)₃OH]₂ | 4-CON[(CH₂)₃OH]₂ | H |
| 43 | CON[(CH₂)₄OH]₂ | 4-CON[(CH₂)₄OH]₂ | H |
| 44 | CON(CH₂CHMeCH₂OH)₂ | 4-CON(CH₂CHMeCH₂OH)₂ | H |
| 45 | CON(CH₂CH₂OH)₂ | 4-CON(CH₂CH₂OH)₂ | 5-OCH₂OMe |
| 46 | CON(CH₂CH₂OH)₂ | 4-CON(CH₂CH₂OH)₂ | 5-N(CH₂CH₂OH)₂ |
| 47 | CON(CH₂CH₂OH)₂ | 4-CON(CH₂CH₂OH)₂ | 5-N(CH₂CH₂OMe)₂ |
| 48 | CON(CH₂CH₂OH)₂ | 4-CON(CH₂CH₂OH)₂ | 5-NMe(CH₂CH₂OH) |
| 49 | CON(CH₂CH₂OH)₂ | 4-N(CH₂CH₂OH)₂ | H |
| 50 | CON(CH₂CH₂OH)₂ | 4-NMe(CH₂CH₂OH) | H |
| 51 | CON(CH₂CH₂OH)₂ | 4-N(CHMeCH₂OH)₂ | H |
| 52 | CON(CH₂CH₂OH)₂ | 4-OCH₂OMe | H |
| 53 | CON(CH₂CH₂OH)₂ | 4-OCHMeOMe | H |
| 54 | CON(CH₂CH₂OH)₂ | 4-OCH₂CH₂OH | H |
| 55 | CON(CH₂CH₂OH)₂ | 4-OCHMeCH₂OH | H |
| 56 | CON(CH₂CH₂OH)₂ | 4-O(CH₂)₃OH | H |
| 57 | CON(CH₂CH₂OH)₂ | 4-O(CH₂)₄OH | H |
| 58 | CON(CH₂CH₂OH)₂ | 3-OCH₂CH₂OH | H |
| 59 | CON(CH₂CH₂OH)₂ | 3-OCHMeCH₂OH | H |
| 60 | CON(CH₂CH₂OH)₂ | 3-OCH₂CH₂NMe₂ | H |
| 61 | CON(CH₂CH₂OH)₂ | 4-SCH₂CH₂OH | H |
| 62 | CON(CH₂CH₂OH)₂ | 4-SO₂CH₂CH₂OH | H |
| 63 | CON(CH₂CH₂OH)₂ | 4-SCH₂CH₂OMe | H |
| 64 | CON(CH₂CH₂OH)₂ | 4-SCHMeCH₂OH | H |
| 65 | CON(CH₂CH₂OH)₂ | 3-SCH₂CH₂OH | H |
| 66 | CON(CH₂CH₂OH)₂ | 4-N(CH₂CH₂OH)₂ | H |
| 67 | CON(CH₂CH₂OH)₂ | 4-NMe(CH₂CH₂OH) | H |
| 68 | CON(CH₂CH₂OH)₂ | 3-N(CH₂CH₂OH)₂ | H |
| 69 | CON(CH₂CH₂OH)₂ | 4-N(CHMeCH₂OH)₂ | H |
| 70 | CON[(CH₂)₃OH]₂ | 4-N(CH₂CH₂OH)₂ | H |
| 71 | CON[(CH₂)₃OH]₂ | 4-OCH₂CH₂OH | H |
| 72 | CON[(CH₂)₃OH]₂ | 4-SCH₂CH₂OH | H |
| 73 | CON[(CH₂)₃OH]₂ | 4-SO₂CH₂CH₂OH | H |
| 74 | CON[(CH₂)₃OH]₂ | 4-NMe(CH₂CH₂OH) | H |
| 75 | OCH₂OMe | 4-SO₂N(CH₂CH₂OH)₂ | H |
| 76 | OCH₂OMe | 4-CON(CH₂CH₂OH)₂ | H |
| 77 | OCH₂CH₂OH | 4-SO₂N(CH₂CH₂OH)₂ | H |
| 78 | OCH₂CH₂OH | 4-CON(CH₂CH₂OH)₂ | H |
| 79 | OCH₂CH₂OH | 4-OCH₂CH₂OH | 5-OCH₂CH₂OH |
| 80 | OCH₂CH₂OH | 5-OCH₂CH₂OH | H |
| 81 | OCH₂CH₂OH | 4-N(CH₂CH₂OH)₂ | H |
| 82 | OCH₂CH₂OH | 4-NMe(CH₂CH₂OH) | H |
| 83 | SO₂CH₂CH₂OH | 5-OCH₂CH₂OH | H |
| 84 | SO₂CH₂CH₂OH | 5-SO₂CH₂OH | H |
| 85 | SO₂CH₂CH₂OH | 4-OCH₂CH₂OH | H |
| 86 | N(CH₂CH₂OH)₂ | 5-N(CH₂CH₂OH)₂ | H |
| 87 | N(CH₂CH₂OH)₂ | 4-N(CH₂CH₂OH)₂ | H |
| 88 | NMe(CH₂CH₂OH) | 5-NMe(CH₂CH₂OH) | H |
| 89 | N(CHMeCH₂OH)₂ | 5-N(CHMeCH₂OH)₂ | H |
| 90 | N(CH₂CH₂OH)₂ | 5-SO₂N(CH₂CH₂OH)₂ | H |
| 91 | N(CH₂CH₂OH)₂ | 5-CON(CH₂CH₂OH)₂ | H |
| 92 | N[(CH₂)₃OH]₂ | 5-N[(CH₂)₃OH]₂ | H |

TABLE 1-continued

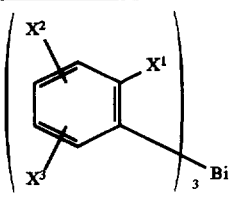

| No. | X¹ | X² | X³ |
|---|---|---|---|
| 93 | N[(CH₂)₂OMe]₂ | 5-N[(CH₂)₂OMe]₂ | H |
| 94 | SO₂N(CH₂CH₂OH)₂ | 5-SO₂N(CH₂CH₂OH)₂ | H |
| 95 | SO₂N(CHMeCH₂OH)₂ | 5-SO₂N(CHMeCH₂OH)₂ | H |
| 96 | SO₂N[(CH₂)₃OH]₂ | 5-SO₂N[(CH₂)₃OH]₂ | H |
| 97 | SO₂N(CH₂CHMeCH₂OH)₂ | 5-SO₂N(CH₂CHMeCH₂OH)₂ | H |
| 98 | SO₂N(CH₂CH₂OH)₂ | 4-O(CH₂)₃OH | 5-O(CH₂)₃OH |
| 99 | SO₂N(CH₂CH₂OH)₂ | 4-OCHMeCH₂OH | 5-OCHMeCH₂OH |
| 100 | SO₂N(CH₂CH₂OH)₂ | 4-SO₂N(CH₂CH₂OH)₂ | 5-N(CH₂CH₂OH)₂ |

The processes of producing the compounds of the present invention will hereinafter be described.

The tris(substituted phenyl)bismuth derivatives represented by the general formula (I) and, if any, the pharmaceutically acceptable salts of the present invention are obtainable, for example, by the method represented by the following reaction scheme.

Reaction scheme (I)

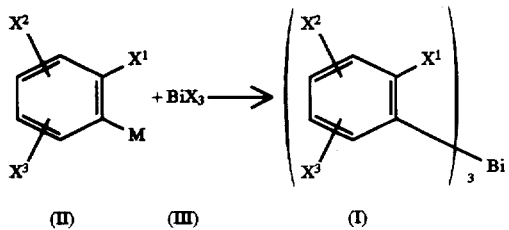

(II)   (III)   (I)

[wherein X¹, X² and X³ are the same as defined above, M is MgX' (wherein X' is an iodine atom, a bromine atom or a chlorine atom) or an alkali metal salt of a lithium atom, a sodium atom or the like, and X is a chlorine atom or a bromine atom)].

The reaction scheme (I) represents a process of producing a compound represented by the general formula (I) of the present invention, which comprises reacting a substituted phenyl metal reactive derivative of the general formula (II) with a trihalobismuth compound of the general formula (III) in an inert solvent.

With respect to the molar ratio of the starting materials in the above reaction, it is satisfactory to use the substituted phenyl metal reactive derivative of the general formula (II) about 3–10 times, preferably about 3.3–5 times as much as the trihalobismuth compound in terms of moles.

The available reaction temperature usually ranges from −40° C. to the boiling point of a solvent used in the reaction when a substituted phenyl magnesium halide is used, and ranges from −78° C. to 40° C. when a substituted phenyl alkali metal salt is used.

As a reaction solvent, ethereal solvents such as diethyl ether, tetrahydrofuran, 1,4-dioxane and diisopropyl ether and mixtures thereof may be used when a substituted phenyl magnesium halide is used, and when a substituted phenyl alkali metal salt is used, in addition to the above-mentioned ethereal solvents, amidic solvents solvents such as N,N-dimethylformamide and N-methylpyrrolidone and mixtures of them with ethereal solvents may be used.

To isolate or purify the compounds of the present invention represented by the general formula (I), techniques known in the field of organic synthesis such as distillation, recrystallization and various chromatographies using silica gel can be employed.

A substituted phenyl metal reactive derivative represented by the general formula (II) is obtainable, for example, by the known processes according to the following reaction schemes (A) and (B) or by utilizing known organic reactions:

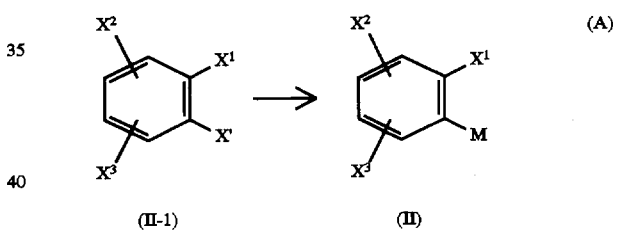

(II-1)   (II)

(wherein X', M, X¹, X² and X³ are the same as defined above)

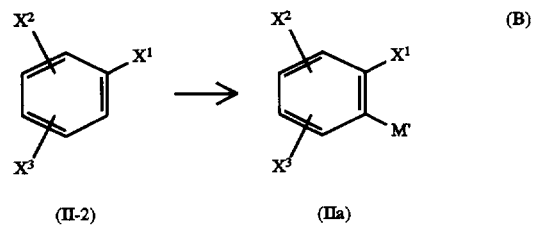

(II-2)   (IIa)

(wherein M' is an alkali metal salt of a lithium atom, a sodium atom or the like, and X¹, X² and X³ are the same as defined above)

The reaction scheme (A), represents a process of producing a substituted phenylmagnesium halide derivative or substituted phenyl alkali metal salt derivative represented by the general formula (II), which comprises reacting a halophenyl derivative of the general formula (II-1) as a starting material, with magnesium or with an alkali metal base such as n-butyllithium, sec-butyllithium, t-butyllithium, phenyllithium or sodium amide to replace the halogen atom by the metal atom.

The reaction temperature for formation of these substituted phenyl metal reactive derivatives is usually between −30° C. and the boiling point of the solvent in the case of a substituted phenylmagnesium halide derivative, and between −78° C. and 0° C. in the case of are substituted phenyl alkali metal salt derivative.

Since in most cases, formation of these substituted phenyl metal reactive derivatives in the reaction system is followed by the reaction with a trihalobismuth compound represented by the reaction scheme (1), almost the same solvent as mentioned for the above reaction scheme (1) are usually used as a solvent in this reaction.

The reaction scheme (B) represents a process for producing a substituted phenyl alkali metal salt derivative of the general formula (IIa), which comprises reacting a phenyl derivative of the general formula (II-2) as a starting material with an alkali metal base to replace the hydrogen atom at the ortho position of the substituent $X^1$ by the alkali metal atom. This process is of great significance in view of production of the starting material, especially when it is difficult to prepare a starting material of the general formula (II-1) which has a halogen atom represented by $X'$ at the ortho position of the substituent $X^1$.

In this process, when the substituent $X^1$ is a sulfonamide type substituent, an amide type substituent or an alkoxy type substituent, the replacement of the hydrogen atom by the alkali metal atom proceeds readily at the desired position.

The above-mentioned conditions for formation of a substituted phenyl alkali metal salt derivative represented by the reaction scheme (A) can almost apply to the reaction condition in this process such as an alkali metal base, the solvent and the temperature, without any problems.

Reaction scheme (2)

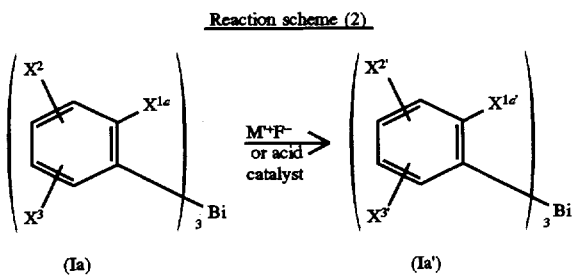

(Ia)  (Ia')

{wherein $X^{1a}$ is $Y^1$—$NR^1R^{2a}$ [wherein $R^{2a}$ is A'—$Z^a$ (wherein A' is an alkylene chain which has 2–6 carbon atoms in total and may have a branch having at least two carbon atoms, and $Z^a$ is $OSiR^4R^5R^6$ (wherein $R^4$, $R^5$ and $R^6$ are the same as defined above), and $Y^1$ and $R^1$ are the same as defined above] or $Y^2$—A—$Z^a$ (wherein $Y^2$, A and $Z^a$ are the same as defined above), $X^2$ and $X^3$ are the same as defined above, $M^+$ is $R^{10}R^{11}R^{12}R^{13}N^+$ (wherein each of $R^{10}$, $R^{11}$,$R^{12}$ and $R^{13}$ is, independently of one another, a $C_{1-4}$ alkyl group), an alkali metal ion or a pyridinium ion, $X^{1a'}$ is any substituent as defined with respect to $X^{1a}$ that has a terminal hydroxyl group, and $X^{2'}$ and $X^{3'}$ are any substituent defined above with respect to $X^2$ and $X^3$, respectively, that has a terminal functional group other than a silyloxy group as Z}.

The reaction scheme (2) represents a process for producing of a tris(o-ω-hydroxyalkylene substituted phenyl) bismuth derivative of the general formal (Ia'), which comprises treating a tris(o-ω-silyloxyalkylene substituted phenyl)bismuth derivative of the general formula (Ia) with a fluoride ion-type compound or with an acid catalyst for desilylation.

In the above reaction, as the fluoride ion-type compound, tetraalkylammonium fluorides such as tetra-n-butylammonium fluoride, alkali metal fluoride salts such as lithium fluoride, sodium fluoride, potassium fluoride and cesium fluoride or pyridinehydrofluoric acid salt may be used.

The molar ratio of the fluoride ion-type compound to the starting material (Ia) may be adjusted properly according to the number of the silyloxy groups in the starting material (Ia). When the starting material (Ia) has more than one silyloxy group, a slightly excessive fluoride compound in relation to the equivalence of the silyl groups is usually enough to eliminate all the silyloxy groups, if desired.

In this reaction, any solvent that does not participate in the reaction may be used, and there is a large choice for the solvent.

With respect to the reaction temperature, in general, the reaction proceeds under relatively mild conditions between −40° C. and room temperature.

An acid catalyst is favorably used in the case of desilylation of a starting material (Ia) having a trialkylsilyl type silyloxy group. In this reaction, an organic solvent may optionally be added to assist dissolution of the starting material (Ia).

In this reaction, as an acid catalyst, mineral acids such as hydrochloric acid and sulfuric acid, organic acids such as citric acid and sulfonic acid derivatives such as p-toluenesulfonic acid and pyridinium p-toluenesulfonic acid, and acid ion exchange resins may be used.

In this reaction, any solvents that does not participate in the reaction can be used, and there is a large choice for the solvent. In particular, a combination of a polar solvent with a non-polar solvent such as an ethanol-dichloromethane mixed solvent, is favorably used because the compound (Ia') separates out after the reaction, due to a large difference in solubility between the compounds (Ia) and (Ia'), thus, is obtainable as crystals.

The reaction temperature is usually adjusted between −10° C. and the boiling point of the solvent.

As the method for isolating or purifying the compound represented by the general formula (Ia') of the present invention, not only recrystallization, various chromatographies using silica gel and liquid chromatography, but also ion-exchange chromatography and affinity chromatography, which are effective particularly when the compound is water soluble, may be mentioned.

The tris(substituted phenyl)bismuth derivatives represented by the general formula (I) and, if any, their pharmaceutically acceptable salts of the present invention may be administered parenterally as an injection, or orally as a tablet, a capsule, a granule, a pill, an emulsion or a suspension.

The above-mentioned pharmaceutical compositions containing the compounds of the present invention contain the compounds of the present invention in an amount of from 1 to 99.5%, preferably 5 to 95% of the total weights for administration in accordance with the pharmaceutical practice.

BEST MODE FOR CARRYING OUT THE INVENTION

Examples (Reference Examples, Synthesis Examples, Formulation Examples and Test Examples)

Now, the present invention will be described in detail with reference to Examples (Reference Examples, Synthesis Examples, Formulation Examples and Test Examples). However, it should be understood that the present invention is by no means restricted to such specific Examples.

In Synthesis Examples, "NMR" and "IR" symbolize "nuclear magnetic resonance spectrum" and "infrared spectrum", respectively. The nuclear magnetic resonance spectra were measured in deuterated chloroform unless otherwise noted.

REFERENCE EXAMPLE 1

N,N-bis(2-trimethylsilyloxyethyl) benzenesulfonamide

To a mixture of 4.97 g of bis(2-trimethylsilyloxylethyl) amine, 3.03 g of triethylamine and 50 ml of benzene, 3.21 g of benzenesulfonyl chloride was added at 0° C. under stirring. After the addition, the mixture was taken out of the cooling bath and stirred further for 2 hours. The reaction mixture was filtered, mixture was taken out of the cooling bath and stirred further for 2 hours. The reaction mixture was filtered, and the filtrate was subjected to vacuum distillation. The residue was passed through a silica gel column with the eluent varying from benzene to benzen-acetic acid (9:1). As a result, 6.23 g of the title compound was obtained as a colorless oily substance. NMRδ: 7.83 (2H,d,J=8.0 Hz),7.52 (3H,m), 3.72, 3.31 (each 4H,t,J=6.5 Hz), 0.09 (18H,s)

REFERENCE EXAMPLE 2 m-(N,N,N',N'-tetrakis(2-t-butyldimethylsilyloxylethyl)benzenedisulfonamide

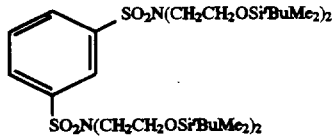

A mixture of 2.31 g of diethanolamine, 11.2 ml of triethylamine and 20 ml of tetrahydrofuran was cooled in an ice water bath, and a solution of 7.23 g of t-butyldimethylsilyl chloride in 30 ml of tetrahydrofuran was added droprise thereto with stirring. After the addition, the mixture was taken out of the bath and stirred overnight. The reaction solution was cooled again to 0° C. and a solution of 2.75 g of m-benzenedisulfonyl chloride in 15 ml of tetrahydrofuran was added droprise. The reaction mixture was taken out of the cooling bath and stirred further for 2 hours. The reaction mixture was filtered, and the filtrate was subjected to vacuum distillation. The resulting residue was purified by silica gel column chromatography by using a benzene-ethyl acetate liquid mixture as the eluent. As a result, 6.7 g of the title compound was obtained as a colorless oily substance. This preparation turns into crystals with a melting point of 55° C. when allowed to stand in the cold.

NMRδ: 8.35 (1H,s), 8.01 (2H,d,J=7.9 Hz), 7.63 (1H,t,J=7.9 Hz), 3.75, 3.36 (each 8H,t,J=6.0 Hz), 0.85 (36H,s), 0.02 (24H,s).

IR$\nu_{max}^{KBr}$cm$^{-1}$: 2953.4, 2856.9, 1583.7, 1464.1, 1352.3, 1253.9, 1110.2, 1001.2, 837.2, 777.4.

EXAMPLE 1

Tris(2-N,N-bis-ethylsulfamoylphenyl)bismuthine ( Compound No. 1)

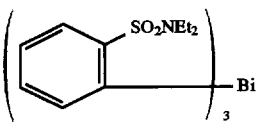

0.853 g of N,N-diethylbenzenesulfonamide was dissolved in 20 ml of tetrahydrofuran, 2.8 ml of a 1.6 M/1 hexane solution of n-butyllithium was added droprise under cooling with dry ice-acetone, and the mixture was stirred for 30 minutes under the same conditions. Then, a solution of 0.315 g of bismuth(III) chloride in 5 ml of tetrahydrofuran was added droprise over 20 minutes, and the mixture was stirred overnight. Water was added little by little to the reaction solution, and the mixture was allowed to separate. The organic layer was separated, and the aqueous layer was extracted with ethyl acetate. The two organic layers were combined, the combined organic layer was washed with saturated aqueous salt solution, and dried over anhydrous sodium sulfate, and then the solvent was distilled off. The resulting residue was purified by silica gel column chromatography by using a n-hexane-ethyl acetate (3:1;v/v) liquid mixture as the eluent. 0.52 g of title compound was separated as crystals with a melting point of 122°–124° C. from the hexane-ethyl acetate liquid mixture.

NMRδ: 8.0 (3H,d), 7.69 (3H,d), 7.48 (3H,t), 7.34 (3H,t), 3.30 (12H,q), 1.15 (18H,t).

IR$\nu_{max}^{KBr}$cm$^{-1}$: 2972.7, 2936.0, 1568.3, 1464.1, 1446.8, 1383.1, 1317.5, 1199.9, 1010.8, 939.4, 733.0, 677.1, 578.7.

EXAMPLE 2

Tris(2-N,N-diethylaminocalbonylphenyl)bismuthine ( Compound No. 2)

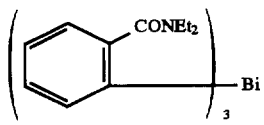

A solution of 5.67 g of N,N-diethylbenzamide in 30 ml of tetrahydrofuran was added droprise to a mixture of 27 ml of a 1.3 M/1 cyclohexane solution of s-BuLi, 4.06 g of N,N, N',N'-tetramethylethylenediamine and 50 ml of tetrahydrofuran over 5 minutes with stirring under cooling with dry ice-acetone. Then, a solution of 2.52 g of bismuth(III) chloride in 15 ml of tetrahydrofuran was added droprise over 15 minutes, and the mixture was stirred overnight at the same temperature. Ice water was carefully poured into the mixture, and after vigorous stirring, the organic layer was separated. The aqueous layer was extracted again with ethyl acetate, and the combined organic layer was washed with a saturated aqueous salt solution and dried over anhydrous sodium sulfate. The solvent was distilled off. The resulting residue was subjected to silica gel column chromatography (eluent: ethyl acetate-n-hexane=1:3 v/v). As a result, 3.30 g of the title compound was obtained as an oily substance.

NMRδ: 7.80 (3H,d), 7.5–7.2 (9H,m), 3.67 (6H,q), 3.38 (6H,brq).

IR$\nu_{max}^{film}$cm$^{-1}$: 2974.6, 1614.6, 1421.7, 1385.0, 1360.3, 1348.7, 1093.8, 742.1.

EXAMPLE 3

Tris(2-methoxymethyloxyphenyl)bismuthine
(Compound No.3)

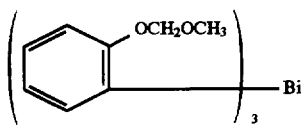

1.38 g of methoxymethyl phenyl ether was dissolved in 50 ml of diethyl ether, and 7.5 ml of a 1.6 M/l hexane solution of n-butyllithium was added dropwise on a dry ice-acetone bath with stirring. The mixture was stirred for 4 hour. Then, a solution of 0.78 g of bismuth(III) chloride in 15 ml of diethyl ether was added dropwise, and the reaction solution was stirred overnight. Iced water was carefully poured into the reaction solution, and after vigorous shaking, the organic layer was separated. The aqueous layer was extracted again with ethyl acetate. After the two organic layers were combined, the combined organic layer was washed with a saturated aqueous salt solution and dried over anhydrous sodium sulfate, and the solvent was distilled off. The resulting residue was purified by silica gel column chromatography (eluent: n-hexane-ethyl acetate=10:1 v/v). The solvent was distilled off, and the residue was separated as crystals from the n;hexane-ethyl acetate. As a result, 0.56 g of the title compound was obtained as crystals with a melting point of 95° C.

NMRδ: 7.53 (3H,d), 7.27 (6H,m), 6.93 (3H,t), 5.14 (6H,s), 3.33 (9H,s).

IR$\upsilon_{max}^{KBr}$cm$^{-1}$: 3049.8, 2901.3, 2361.2, 1570.2, 1456.4, 1435.2, 1224.9, 1186.4, 1149.7, 1113.1, 1072.6, 1007.0, 918.2, 748.5.

EXAMPLE 4

Tris(2-N,N-bis(2-hydroxyethyl)sulfamoylphenyl)
bismuthine (Compound No.4)

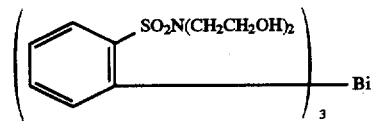

1.56 g of the N,N-bis(2-trimethylsilyloxyethyl) benzenesulfonamide preparation obtained in Reference Example 1 was dissolved in 20 ml of tetrahydrofuran, and a 1.6 M/l hexane solution of n-butyllithium was added dropwise with stirring on a dry ice-acetone cooling bath. The mixture was stirred for 1 hour at the same temperature, and a solution of 0.32 g of bismuth(III) chloride in 10 ml of tetrahydrofuran was added droprise. Then, the reaction solution was stirred overnight. Ice water was carefully poured into the reaction solution, and it was stirred further at room temperature for 24 hours. The solvent in the reaction mixture was distilled off, and the resulting residue was crystallized from the water-ethernol, as a result, 0.49 g of the title compound was obtained as crystals with a melting point of 183° C.

NMR (acetone-d$_6$)δ: 8.12 (3H,d), 7.72 (3H,d), 7.64 (3H,dd), 7.47 (3H,dd), 4.26 (6H,t,disappeared upon addition of deutrium), 3.76 (12H,q), 3.42(12H,t).

EXAMPLE 5

Tris (2,4-bis (N,N-bis(2-t-butyldimethylsilyloxyethyl)sulfamoyl)phenyl) bismuthine (Compound No.5)

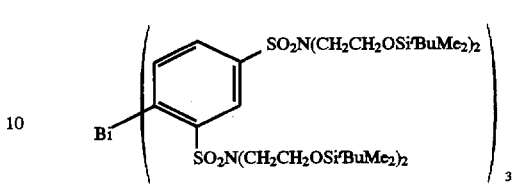

23.45 g of the m-(N,N,N',N'-tetrakis(2-t-butyldimethylsilyloxyethyl)benzenedisulfonamide preparation prepared in Reference Example 2 was dissolved in 234 ml of tetrahydrofuran, and 20.0 ml of a 1.6 M/l n-hexane solution of n-BuLi was added droprise with stirring on a dry ice-acetone cooling bath. After 1 hour of stirring, a solution of 2.16 g of bismuth(III) chloride in 21 ml of tetrahydrofuran was added droprise. After the addition, it was stirred overnight. 166 ml of ice water was carefully poured into the reaction solution, and after the mixed solution was shaked vigorously, the tetrahydrofuran layer was separated. The aqueous layer was extracted again with ethyl acetate. After the two organic layers were combined, the combined layer was washed with saturated aqueous salt solution and dried over anhydrous sodium sulfate, and the solvent was distilled off to obtain 24.9 g of a crude product. It was dissolved in 74.7 g of a mixed solvent of ethanol: methanol=1:1 at 50° C., and the solution was cooled to −10° C. The resulting crystals were collected by filtration and dried. As a result, 13.59 g of the title compound was obtained as crystals with a melting point of 115° C. (yield 70.5%).

NMR (acetone-d$_6$)δ: 8.36 (3H,s), 7.75 (6H,dd), 3.80–3.69 (24H,m), 3.48 (12H,t), 3.32 (12H,t), 0.87 (108H,s), 0.02 (72H,s).

IR$\upsilon_{max}^{KBr}$cm$^{-1}$: 2957.2, 2930.2, 2858.9, 1473.8, 1361.9, 1336.8, 1257.7, 1170.9, 1105.3, 1001.2.

EXAMPLE 6

Tris(2,4-bis(N,N-bis(2-hydroxyethyl)sulfamoyl) phenyl)bismuthine (Compound No.6)

1) 13.59 g of the tris(2,4-bis(N,N-bis(2-t-butyldimethylsilyloxyethyl)sulfamoyl)phenyl)bismuthine preparation prepared in Example 5 was dissolved in a mixed solvent containing 13.6 ml of ethanol and 27 ml of dichloromethane, and 0.272 g of p-toluenesulfonic acid monohydrate was added thereto. The mixture was refluxed under heating at 50° C. for 6 hours, and then cooled to room temperature. The crystals were collected by filtration, washed with 29.5 ml of dichloromethane and dried. As a result, 5.54 g of the title compound was obtained as crystals with a melting point of 110°–113° C.

NMR (D$_2$O)δ: 8.49 (3H,s), 7.38, 6.82 (each 3H,A Bq), 3.65 (24H,m), 3.44 (12H,t), 3.29 (12H,t).

2) A solution of 1.38 g of the tris(2,4-bis(N,N-bis(2-t-butyldimethylsilyloxyethyl)sulfamoyl)phenyl)bismuthine preparation obtained in Example 5 in 15 ml of tetrahydrofuran was cooled to −30° C., and 5.88 ml of a 1 M/1 tetrahydrofuran solution of tetra-n-butylammonium fluoride was gradually added droprise under stirring. After removal of the cooling bath, it was stirred further for 2 hours. Water and n-hexane were added to the reaction solution, and after vigorous shaking, the aqueous layer was separated out. The aqueous layer was washed with chloroform three times, and lyophilized. As a result, 0.67 g of the title compound as obtained. NMR (D$_2$O)δ: 8.49 (3H,s), 7.38, 6.82 (each 3H,A Bq), 3.65 (24H,m), 3.44 (12H,t), 3.29(12H,t)

FORMULATION EXAMPLE 1

| Tablet | |
|---|---|
| Compound No. 1 | 20 g |
| Lactose | 10 g |
| Starch | 4 g |
| Starch (for glue) | 1 g |
| Magnesium stearate | 0.1 g |
| Calcium carboxylmethylcellulose | 7 g |
| Total | 42.1 g |

The above ingredients are mixed by a conventional method, and the mixture is formed into sugar-coated tablets containing 500 mg of the active ingredient per tablet.

FORMULATION EXAMPLE 2

| Capsule | |
|---|---|
| Compound No. 3 | 20 g |
| Lactose | 10 g |
| Cellulose crystallites | 10 g |
| Magnesium stearate | 1 g |
| Total | 41 g |

The above ingredients are mixed in a conventional method, and the mixture was stuffed into gelatin capsules to prepare capsules containing 500 mg of the active ingredient per capsule.

FORMULATION EXAMPLE 3

| Injection | |
|---|---|
| Compound No. 6 | 450 g |
| Distilled water for injection | appropriate amount |
| Total | 1000 ml |

TEST EXAMPLE 1

(Test on X-Ray Radiographic Contrasting Ability)

A 55 w/v % aqueous solution of compound No.6 was used in in vitro X-ray CT. As a result, it was observed that it had an X-ray radiographic contrasting ability comparable to that of a 15 w/v % iopamidol solution (X-ray acceleration voltage 80 kv, sample layer length 4 mm).

| Compound | CT-M value |
|---|---|
| Compound No. 6 (55 w/v%) | 2,764 |
| Iopamidol | 3,085 |

TEST EXAMPLE 2

(Toxicity Test)

Compound No.6 was dissolved in physiological saline for injection to prepare an administration solution with a concentration of 28.5 w/v %.

The solution was administered to four ICR male mice (six weeks old) at a rate of 1 ml/min by intravenous injections on tail at a doze of 11.4 g/kg. Within 5 minuets of the administration, reduction in the voluntary motions of all mice were observed, however, three mice recovered in 30 minutes, and one in 2 hours. Thereafter, no special symptoms to mention were observed for 7 days. None of the mice died.

TEST EXAMPLE 3

(Oil-Water Partition Coefficient)

The oil-water partition coefficient of compound No.6 between 1-octanol and water was measured in accordance with the method described in Acta Radiologica, 370, 33–36 (1987), and found to be P=0.00199. This means a high hydrophilisity of the compound comparable to or higher than that of iopamidol, which has a partition coefficient of 0.0025 according to the above-mentioned reference.

As is evident from these results, the compounds of the present invention has an excellent radiographic contrasting ability, and, particularly, those which are water soluble exhibit sufficient contrasting ability. Therefore, the compounds of the present invention can provide improved, safe and useful contrast media for injection which have low osmotic pressures and low viscosities and are used for X-radiography of the vasculature, the urinary tract, the gallbladder, the bile duct or the cerebrospinal cavity.

We claim:

1. A tris(substituted phenyl) bismuth compound of the general formula (I), or a pharmaceutically acceptable salt thereof:

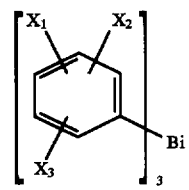

wherein:

$X^1$ is:
  $Y^1$—$NR^1R^2$,
  O—CH($R^7$)—$OR^9$, or
  $Y^2$—A—Z, $Y^1$ is:
  —$SO_2$— or —C(O)—, $R^1$ and $R^2$ are:
  independently, a hydrogen atom, $C_{1-4}$ alkyl, or A—Z, with the proviso that $R^1$ and $R^2$ cannot both be hydrogen, A is:
  an alkylene chain which has 2–6 carbon atoms in total and may have a branch having at least two carbon atoms, Z is:
  $OR^3$, or
  $NR^7R^8$, $R^3$ is:
  $SiR^4R^5R^6$,
  H, or
  $C_{1-4}$ alkyl $R^4$, $R^5$ and $R^6$ are:
  independently, $C_{1-4}$ alkyl or phenyl, $R^7$ and $R^8$ are:

independently, hydrogen or $C_{1-4}$ alkyl, $R^9$ is:
  $C_{1-4}$ alkyl, $Y^2$ is:
  $O$, $-S(O)_n-$ or $-\underset{R^1}{N}-$ n is:
  an integer of 0 or 2, and each of $X^2$ and $X^3$ is, independently, hydrogen or $X^1$.

2. A tris(substituted phenyl) bismuth compound or the pharmaceutically acceptable salt thereof as set forth in claim 1, wherein $X^1$ is:
  $Y^1-NR^1R^2$, or
  $-O-CH(R^7)-OR^9$, $Y^1$ is:
  $-SO_2-$, $R^1$ is:
  independently of $R^2$, a $C_{1-4}$ alkyl group or $A-Z^1$, $R^2$ is:
  independently of $R^1$, a $C_{1-4}$ alkyl group, or $A-Z^1$, A is:
  an alkylene chain which has 2–6 carbon atoms in total and may have a branch having at least two carbon atoms, $Z^1$ is:
  $OR^3$, $R^3$ is:
  $SiR^4R^5R^6$,
  H, or
  $C_{1-4}$ alkyl, $R^4$, $R^5$ and $R^6$ are:
  independently, $C_{1-4}$ alkyl or phenyl, $R^7$ is:
  H, or $C_{1-4}$ alkyl, $R^9$ is: $C_{1-4}$ alkyl, and each of $X^2$ and $X^3$ is, independently, a hydrogen atom or $X^1$.

3. A process of producing the tris(substituted phenyl) bismuth compound, or the pharmaceutically acceptable salt thereof according to claim 1, which comprises reacting a substituted phenyl metal reactive compound of the formula (II)

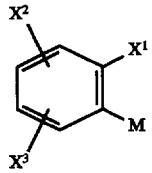
(II)

wherein $X^1$ is:
  $Y^1-NR^1R^2$,
  $O-CH(R^7)-OR^9$, or
  $Y^2-A-Z$, $Y^1$ is:
  $-SO_2-$ or $-C(O)-$, $R^1$ is:
  independently of $R^2$, hydrogen, $C_{1-4}$ alkyl, or $A-Z$, $R^2$ is:
  independently of $R^1$, hydrogen, $C_{1-4}$ alkyl, or $A-Z$, with the proviso that $R^1$ and $R^2$ cannot both be hydrogen, A is:
  an alkylene chain which has 2–6 carbon atoms in total and may have a branch having at least two carbon atoms, Z is:
  $OR^3$, or
  $NR^7R^8$, $R^3$ is:
  $SiR^4R^5R^6$,
  H, or
  $C_{1-4}$ alkyl, $R^4$, $R^5$ and $R^6$ are:
  independently, $C_{1-4}$ alkyl or phenyl, $R^7$ is:
  independently of $R^8$, a hydrogen atom or a $C_{1-4}$ alkyl group, $R^8$ is:
  independently of $R^7$, a hydrogen atom or a $C_{1-4}$ alkyl group, $R^9$ is:
  a $C_{1-4}$ alkyl group, $Y^2$ is:
  $O$, $-S(O)_n-$ or, $-\underset{R^1}{N}-$ n is:
  an integer of 0 or 2, and each of $X^2$ and $X^3$ is, independently, a hydrogen atom or $X^1$, M is:
  $MgX'$, or an alkali metal base, and $X'$ is:
  an iodine atom, a bromine atom or a chlorine atom, with a trihalobismuth compound of the general formula (III):

$$BiX_3 \qquad\qquad (III)$$

wherein X is a chlorine atom or a bromine atom.

4. A process of producing the tris(O-ω-hydroxyalkoxylene substituted phenyl) bismuth compound or the pharmaceutically acceptable salt thereof as set forth in claim 1, comprising treating a tris(O-ω-silyloxyalkylene substituted phenyl) bismuth compound of the formula (Ia):

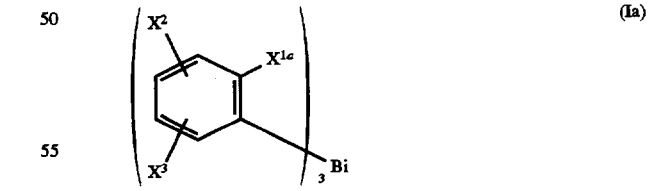
(Ia)

wherein:

$X^{1a}$ is:
  $Y^1-NR^1R^{2a}$, or
  $Y^2-A-Z^a$, $Y^1$ is:
  $-SO_2-$ or $-C(O)-$, $R^1$ is:
  a hydrogen atom, a $C_{1-4}$ alkyl group or $A-Z$, $R^{2a}$ is:
  $A^1-Z^a$, A is: an alkylene chain which has 2–6 carbon atoms in total and may have a branch having at least two carbon atoms, $A^1$ is:
an alkylene chain which has 2–6 carbon atoms in total and may have a branch having at least two carbon atoms, Z is:
$OR^3$, or $NR^7R^8$ $Z^a$ is:
$OSiR^4R^5R^6$, $R^3$ is:
$SiR^4R^5R^6$,
H, or
$C_{1-4}$ alkyl, $R^4$, $R^5$ and $R^6$ are:
independently, $C_{1-4}$ alkyl or phenyl, $R^7$ and $R^8$ are:
independently, hydrogen or $C_{1-4}$ alkyl, $Y^2$ is:

O, $-S(O)_n$, or 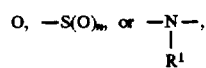

n is:
an integer of 0 or 2.

$X^2$ and $X^3$ are:
independently,
H,
$Y^1-NR^1R^2$,

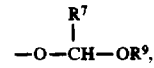

$Y^2-A-Z$,
wherein
$R^1$ and $R^2$ are, independently, a hydrogen atom, a $C_{1-4}$ alkyl group or A—Z, with the proviso that $R^1$ and $R^2$ can not both be hydrogen, $R^9$ is:
$C_{1-4}$ alkyl, with (i) a fluoride ion-type compound of the general formula (IV)

$$M^{1+}F^- \qquad\qquad (IV),$$

wherein $M^{1+}$ is a quaternary ammonium ion represented by $R^{10}R^{11}R^{12}R^{13}N^+$, wherein each of $R^{10}$, $R^{11}$, $R^{12}$ and $R^{13}$ is, independently, a $C_{1-4}$ alkyl group, or $M^{1+}$ is an alkali metal ion or pyridinium ion, or (ii) an acid catalyst, for desilylation.

5. A radiographic contrast medium containing the tris (substituted phenyl) bismuth compound or the pharmaceutically acceptable salt thereof as set forth in claim 1.

6. The tris(substituted phenyl) bismuth compound as set forth in claim 1, wherein said compound is tris(2-N,N-bis-ethylsulfamoylphenyl)bismuthine.

7. The tris(substituted phenyl) bismuth compound as set forth in claim 1, wherein said compound is tris(2-N,N-diethylaminocarbonylphenyl)bismuthine.

8. The tris(substituted phenyl) bismuth compound as set forth in claim 1, wherein said compound is tris(2-methoxymethyloxyphenyl)bismuthine.

9. The tris(substituted phenyl) bismuth compound as set forth in claim 1, wherein said compound is tris(2-N,N-bis (2-hydroxyethyl)sulfamoylphenyl)bismuthine.

10. The tris(substituted phenyl) bismuth compound as set forth in claim 1, wherein said compound is tris(2,4-bis(N,N-bis(2-t-butyldimethylsilyloxyethyl)sulfamoyl)phenyl) bismuthine.

11. The tris(substituted phenyl) bismuth compound as set forth in claim 1, wherein said compound is tris(2,4-bis(N,N-bis(2-t-butyldimethylsilyloxyethyl)sulfamoyl)phenyl) bismuthine.

* * * * *